United States Patent
Maloney

(10) Patent No.: US 8,157,755 B2
(45) Date of Patent: Apr. 17, 2012

(54) MOVABLE JOINT HAVING UP TO SIX DEGREES OF FREEDOM

(75) Inventor: Geoff Maloney, Geelong (AU)

(73) Assignee: Pod I.P. Pty Ltd, Geelong (AU)

(*) Notice: Subject to any disclaimer, the term of this patent is extended or adjusted under 35 U.S.C. 154(b) by 602 days.

(21) Appl. No.: 11/791,057

(22) PCT Filed: Nov. 18, 2005

(86) PCT No.: PCT/AU2005/001755
§ 371 (c)(1),
(2), (4) Date: Apr. 2, 2008

(87) PCT Pub. No.: WO2006/053391
PCT Pub. Date: May 26, 2006

(65) Prior Publication Data
US 2009/0030356 A1 Jan. 29, 2009

(30) Foreign Application Priority Data
Nov. 19, 2004 (AU) .................................. 2004906657

(51) Int. Cl.
*A61F 5/00* (2006.01)
(52) U.S. Cl. .................. 602/16; 602/5; 602/23; 602/26; 602/27
(58) Field of Classification Search .................. 602/2, 5, 602/16, 20, 23, 26, 27–29; 623/18, 20, 21, 623/39; D24/190
See application file for complete search history.

(56) References Cited

U.S. PATENT DOCUMENTS

| | | | |
|---|---|---|---|
| 4,634,445 A | 1/1987 | Helal | |
| 5,086,760 A | 2/1992 | Neumann et al. | |
| 5,534,033 A | 7/1996 | Simpson | |
| 5,823,931 A | 10/1998 | Gilmour | |
| 2002/0107464 A1 | 8/2002 | Castillo | |
| 2003/0083602 A1 | 5/2003 | Haaland | |
| 2004/0002376 A1 | 1/2004 | Swift et al. | |
| 2004/0054311 A1 | 3/2004 | Sterling | |
| 2004/0153015 A1 | 8/2004 | Seligman et al. | |

FOREIGN PATENT DOCUMENTS

| | | |
|---|---|---|
| JP | 9-103443 A | 4/1997 |
| JP | 09103443 A | 4/1997 |
| JP | 11500018 A | 1/1999 |
| WO | WO 2004/002376 A1 | 1/2004 |

OTHER PUBLICATIONS

Japanese Office Action dated Oct. 18, 2011 for corresponding Japanese application 2007-541582.

*Primary Examiner* — Kim M Lewis
(74) *Attorney, Agent, or Firm* — Wolf, Greenfield & Sacks, P.C.

(57) ABSTRACT

A movable joint (100) including: a body (102) having two spaced apertures (104, 106) connected by an opening (108); two arms (110, 112) having ends receivable in the apertures; and a resilient connector (114) passing though the opening (108) to connect the ends of the arms in the apertures, wherein the resilience of the resilient connector: allows independent movement of the arms in up to six degrees of freedom which is controlled by engagement of abutment portions (120) of the arms (110, 112) with respective abutment portions (122) of the apertures (104, 106); and absorbs force applied to the arms.

19 Claims, 8 Drawing Sheets

MOVABLE JOINT HAVING UP TO SIX DEGREES OF FREEDOM

FIELD OF THE INVENTION

The present invention relates to a movable joint having up to six degrees of freedom.

BACKGROUND OF THE INVENTION

Complex movable joints, such as the human knee joint, allow relative movement of two parts in six degrees of freedom. Six degrees of freedom refers to movement relative to three orthogonally opposed axes, plus rotation about each of those three axes.

Previously proposed movable joints having more than one degree of freedom typically connect two parts by pins that are pivotable and angularly movable in fixed slots. Such pin-in-slot movable joints cannot simulate the natural anatomical movement of human or animal joints in up to six degrees of freedom. In addition, the rigidity of pin-in-slot movable joints means they are unable to absorb shocks, vibrations and loads applied to them.

A need therefore exists for a simple, low cost movable joint having up to six degrees of freedom which is capable of absorbing shocks, vibrations and loads. Such a movable joint has many potential uses, for example, use in human or animal joint support devices.

SUMMARY OF THE INVENTION

According to the present invention, there is provided a movable joint including:
- a body having two spaced apertures connected by an opening;
- two arms having ends receivable in the apertures; and
- a resilient connector passing through the opening to connect the ends of the arms in the apertures, wherein the resilience of the resilient connector:
  - allows independent movement of the arms in up to six degrees of freedom which is controlled by engagement of abutment portions of the arms with respective abutment portions of the apertures; and
  - absorbs forces applied to the arms.

The present invention also provides a movable joint system including:
- a plurality of bodies each having two spaced apertures connected by an opening;
- two arms having ends receivable in the apertures; and
- a resilient connector passing through the opening to releasably connect the ends of the arms in the apertures, wherein the resilience of the resilient connector:
  - allows independent movement of the arms in up to six degrees of freedom which is controlled by engagement of abutment portions of the arms with respective abutment portions of the apertures; and
  - absorbs forces applied to the arms;
- wherein the abutment portions of the apertures of each body are differently shaped to the abutment portions of the apertures of other bodies, whereby the independent movement of the arms in up to six degrees of freedom is selectively controllable by interchanging the bodies.

The present invention further provides a joint support device for a human or animal joint including two support portions which are connected for relative movement about the human or animal joint by at least one movable joint of the present invention and/or by the movable joint system of the present invention.

BRIEF DESCRIPTION OF THE DRAWINGS

Embodiments of the present invention will now be described solely by way of non-limiting examples and with reference to the accompanying drawings in which.

DETAILED DESCRIPTION OF THE EMBODIMENTS

Figure 1:
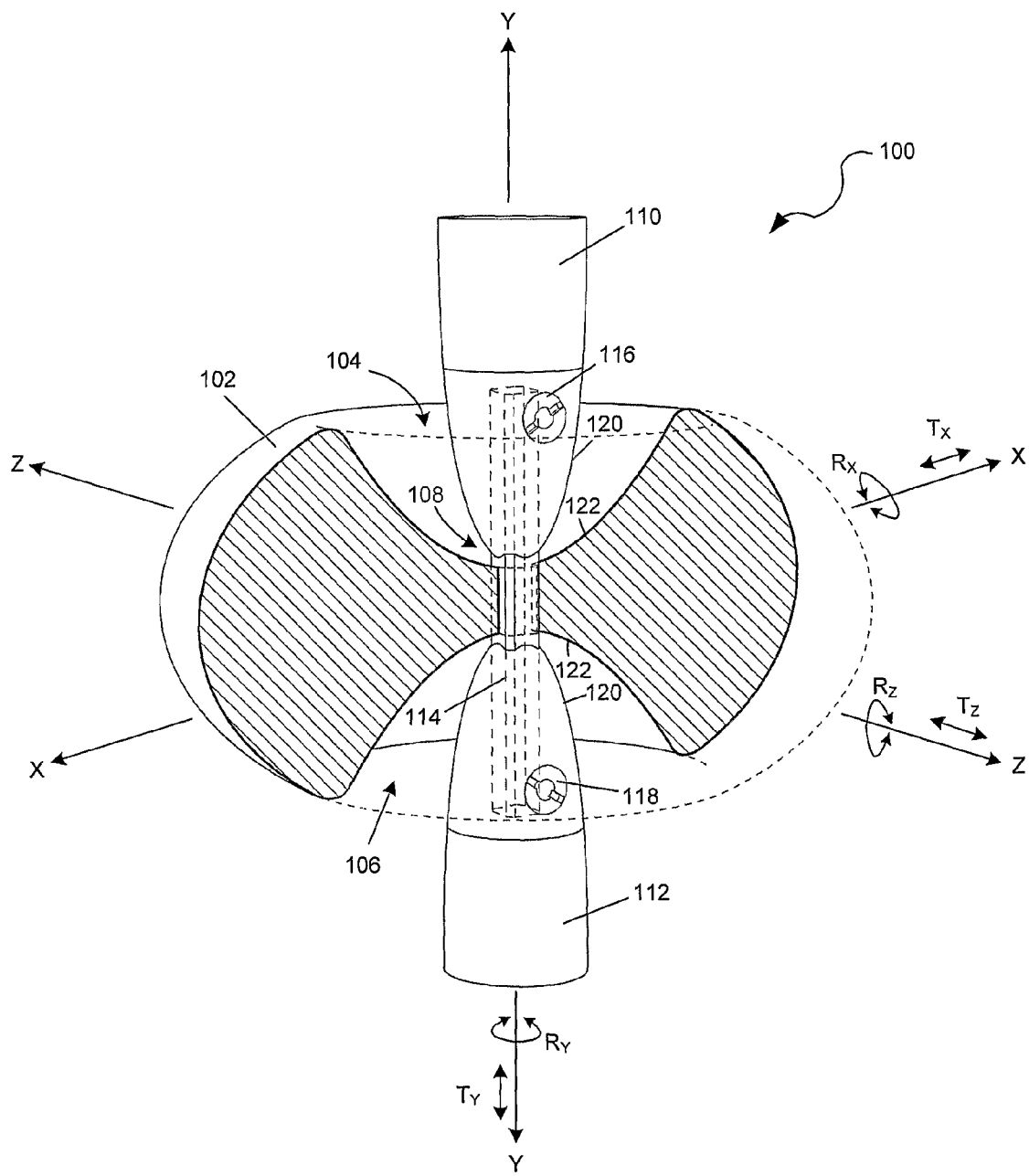
FIG. 1 is a schematic partial cross-sectional perspective view of a generic embodiment of a movable joint of the present invention.

FIG. 1 illustrates a generic embodiment of a movable joint 100 of the present invention. The movable joint 100 includes a body 102 having two spaced apertures 104, 106 connected by an opening 108, as depicted in the cross-section of the body 102. The size, shape and spacing of the apertures 104, 106 will vary for any particular application. Two arms 110, 112 have ends receivable in, and at least partially abutting, the apertures 104, 106. The size and shape of the abutting ends of the arms 110, 112 will also vary for any particular application. The body 102 and/or the arms 110, 112 can be manufactured by, for example, injection moulding. The body 102 and/or the arms 110, 112 can be manufactured from, for example, polymeric materials, such as polyurethanes, silicones, polyethylenes, nylons, polyesters, and polyester elastomers, and combinations thereof. The polymeric materials can include reinforcements such as glass cloth or fibres, graphite fibres, Kevlar (trade mark) fibres and Spheretex (trade mark) fibres. Other suitable manufacturing methods and materials will be apparent to those skilled in the art.

Figure 2:
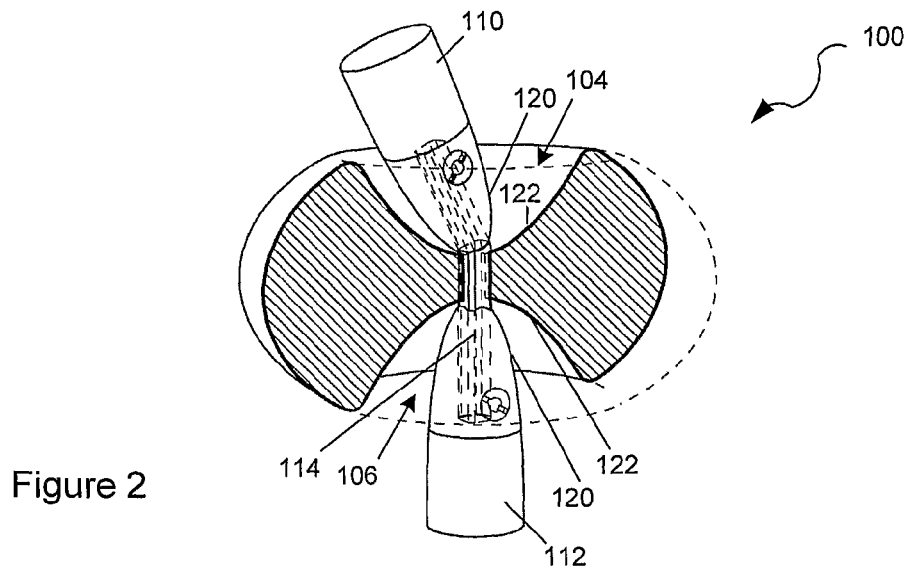
FIGS. 2-4 are schematic partial cross-sectional perspective views of the movable joint of FIG. 1 at various positions of movement in up to six degrees of freedom.
Figure 3:
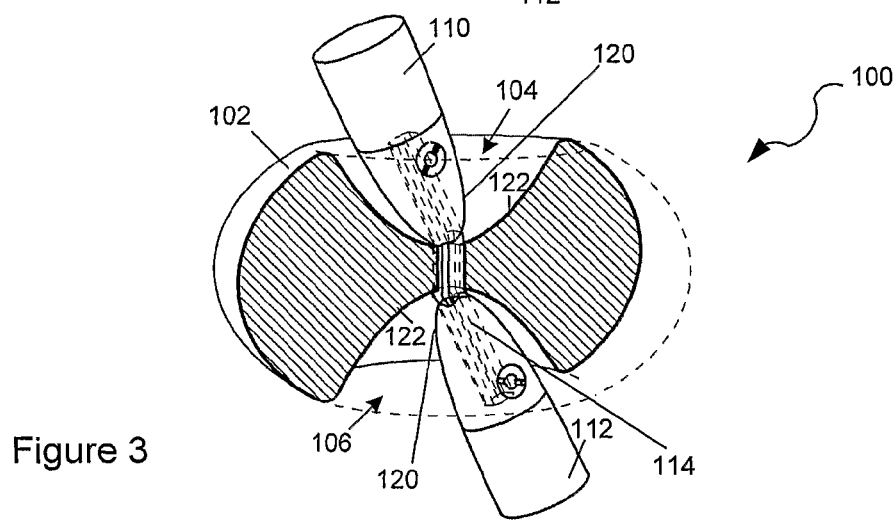
Figure 4:
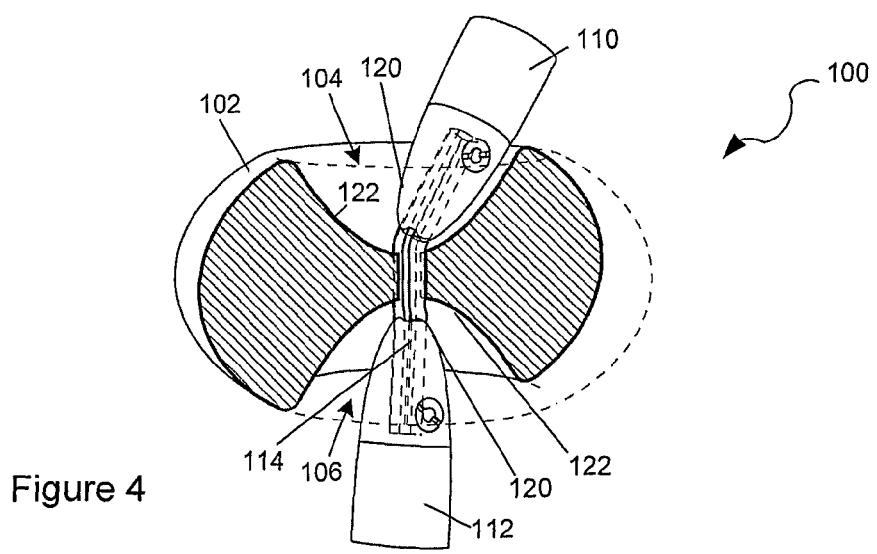

A resilient connector 114 illustrated in phantom in FIG. 1 passes through the opening 108 and connects the ends of the arms 110, 112 in the apertures 104, 106. The resilient connector 114 is releasably connected to the ends of the arms 110, 112 by releasable fasteners 116, 118, for example, screws. In use, the resilience of the resilient connector 114 allows independent movement of the arms 110, 112 in up to six degrees of freedom which is controlled by engagement of abutment portions 120 of the arms 110, 112 with respective abutment portions 122 of the apertures 104, 106. In FIG. 1, three orthogonal axes X, Y, Z provide a reference direction for each of the six degrees of freedom of movement. The six degrees of freedom of the arms 110, 112 include three translation degrees $T_X$, $T_Y$, $T_Z$ and three rotational degrees $R_X$, $R_Y$, $R_Z$. FIGS. 2-4 illustrate various example positions of the arms 110, 112 in movement with six degrees of freedom. Also during use, the resilience of the resilient connector 114 absorbs forces applied to the arms 110, 112 such as shocks, vibrations and loads. Depending on the resilience characteristics of the resilient connector 114, external tensile, compressive and/or torsional forces and loads applied to the arms 110, 112 may be dampened, absorbed or resisted.

Figure 5:
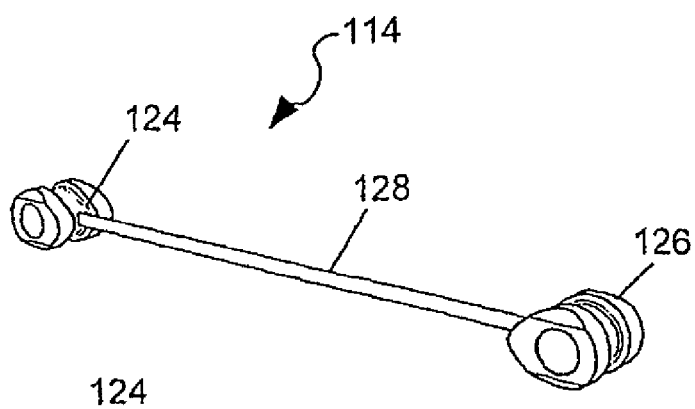
FIGS. 5-8 are schematic perspective views of embodiments of a resilient connector of the movable joint of the present invention.
Figure 6:
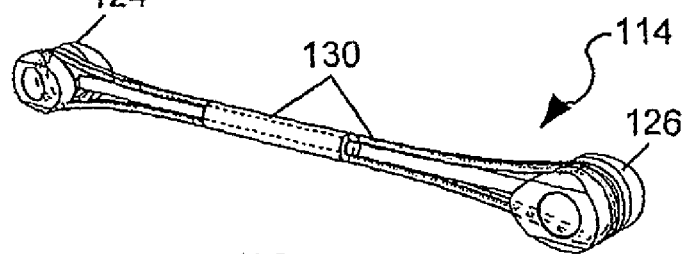
Figure 7:
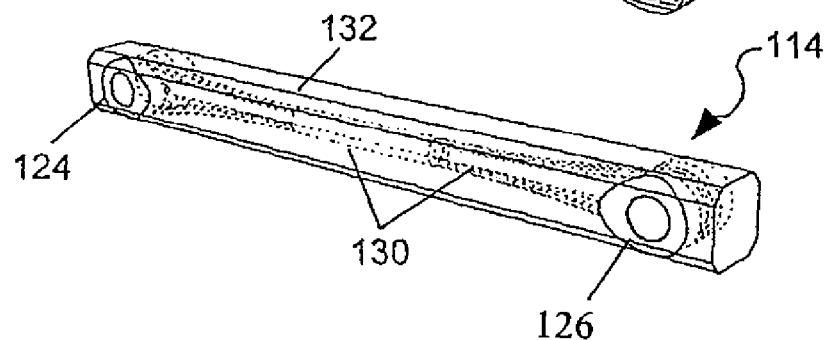
Figure 8:
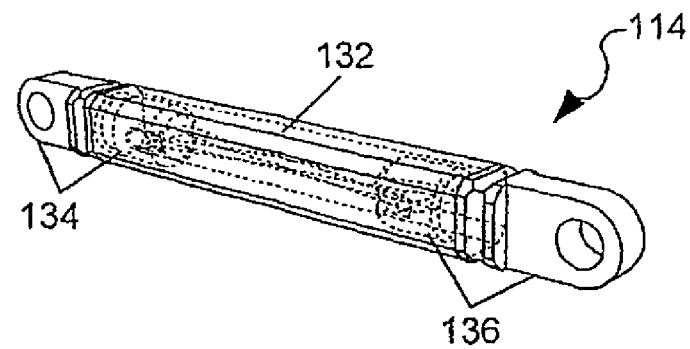

FIGS. 5-7 illustrate sequential steps in the manufacture of one embodiment of the resilient connector 114. Manufacture of this embodiment starts with an integral assembly of two spaced spools 124, 126 connected by a spacer 128. The integral assembly of the spools 124, 126 and the spacer 128 is then placed in jig (not shown), and a pretensioned spine 130 is formed by winding fibre around and between the spools 124, 126 both longitudinally and radially relative to the spacer 128, as depicted in FIG. 6. A resilient member 132 is then moulded over the spools 124, 126 and the pretensioned spine 130. The spools 124, 126 have transverse through-holes for receiving fasteners to connect the resilient connector 114 to the arms 110, 112. In use, the pretensioned spine 130 resists tensile loads applied to the arms 110, 112. Apart from facilitating easy manufacture, the spacer 128 can provide a degree of stiffness in the manufactured resilient connector 114. FIG. 8 illustrates an alternative embodiment of the resilient connector 114. In this embodiment, the pretensioned spine 130 is formed by tying fibre between inner portions of the two end-plugs 134, 136. The resilient member 132 is then moulded over inner portions of the end-plugs 134, 136 and the pretensioned spine 130. The outer portions of the end-plugs 134, 136 have transverse through-holes for receiving fasteners to connect the resilient connector 114 to the arms 110, 112.

The spools 124, 126 and/or the spacer 128 can be made by, for example, injection moulding. The spools 124, 126 and/or the spacer 128 can be made from, for example, polymeric materials, such as polyurethanes, silicones, polyethylenes, nylons, polyesters, and polyester elastomers, and combinations thereof. The polymeric materials can include reinforcements such as glass cloth or fibres, graphite fibres, Kevlar (trade mark) fibres and Spheretex (trade mark) fibres. The end-plugs 134, 136 can be made from, for example, stainless steel. The pretensioned spine 130 can be made from, for example, natural or synthetic fibres having high tensile strength, flex fatigue resistance, and low creep. Suitable materials include: polyester or liquid crystal polymer fibres, such as Vectran (trade mark) fibre; aramid fibres, such as Kevlar (trade mark) fibre; ultra-high molecular weight polyethylene fibres, such as Dyneema (trade mark) fibre or Spectra (trade mark) fibre; and natural fibres, such as hemp. The resilient member 132 can be made from, for example, transparent thermoplastic polyurethane so that the integrity of the pretensioned spine 130 can be visually inspected. Other suitable manufacturing methods and materials will be apparent to those skilled in the art.

The generic movable joint 100 can be customised for any particular application by controlling the geometry of the apertures 104, 106 and/or the abutting ends of the arms 110, 112, and/or by controlling the resilience characteristics of the resilient connector 114. Specifically, independent movement of the arms 110, 112 in up to six degrees of freedom may be controlled by selection of the respective three-dimensional shape of the abutment portions 120, 122 of the arms 110, 112 and/or the apertures 104, 106, and/or by selection of the resilience characteristics of the resilient connector 114. For example, the independent movement of the arms in six degrees of freedom may be controlled to substantially simulate anatomical movement of a human or animal joint in up to six degrees of freedom.

Figure 9:
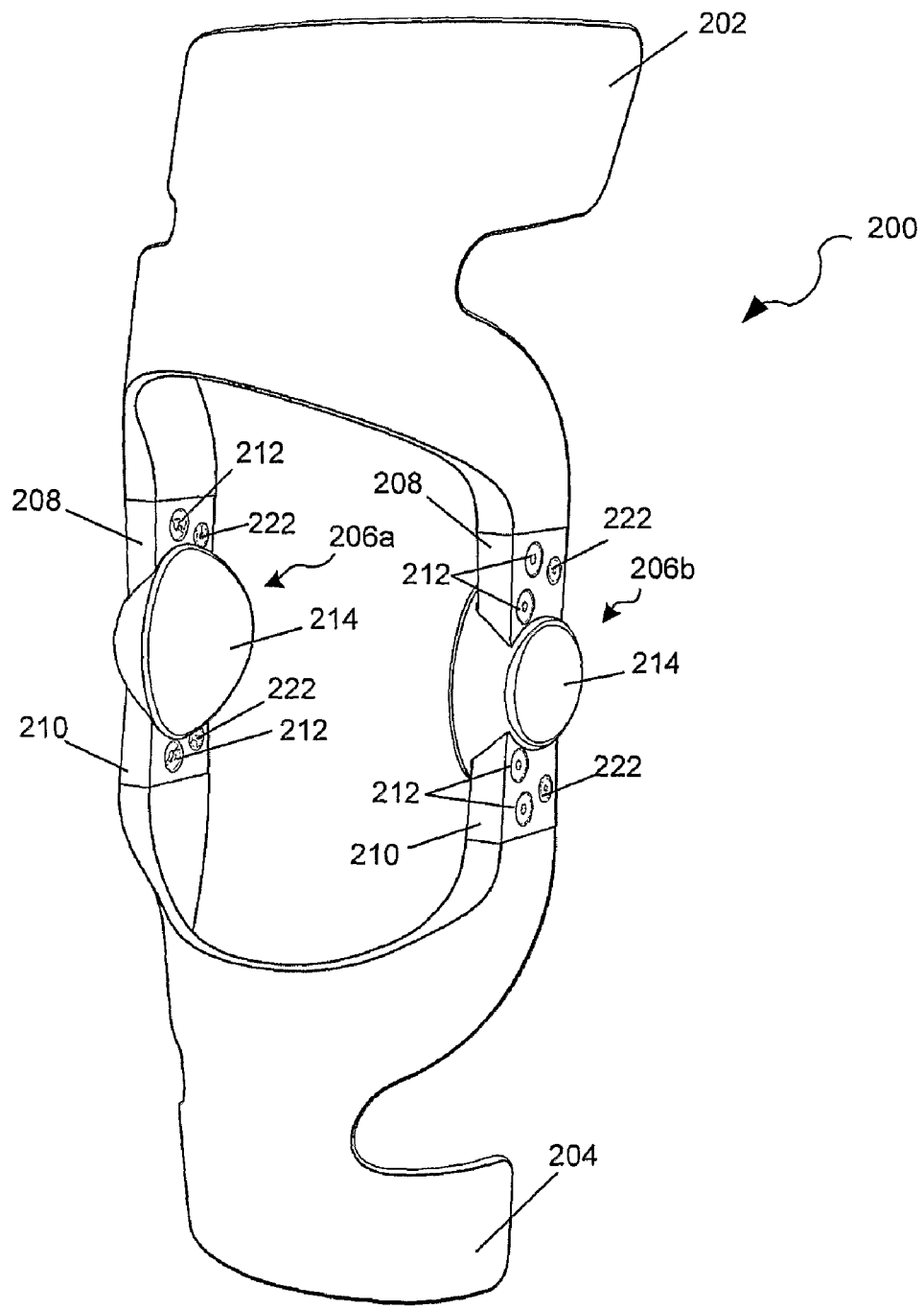
FIG. 9 is a schematic perspective view of a knee brace including embodiments of a movable joint of the present invention.
Figure 10:
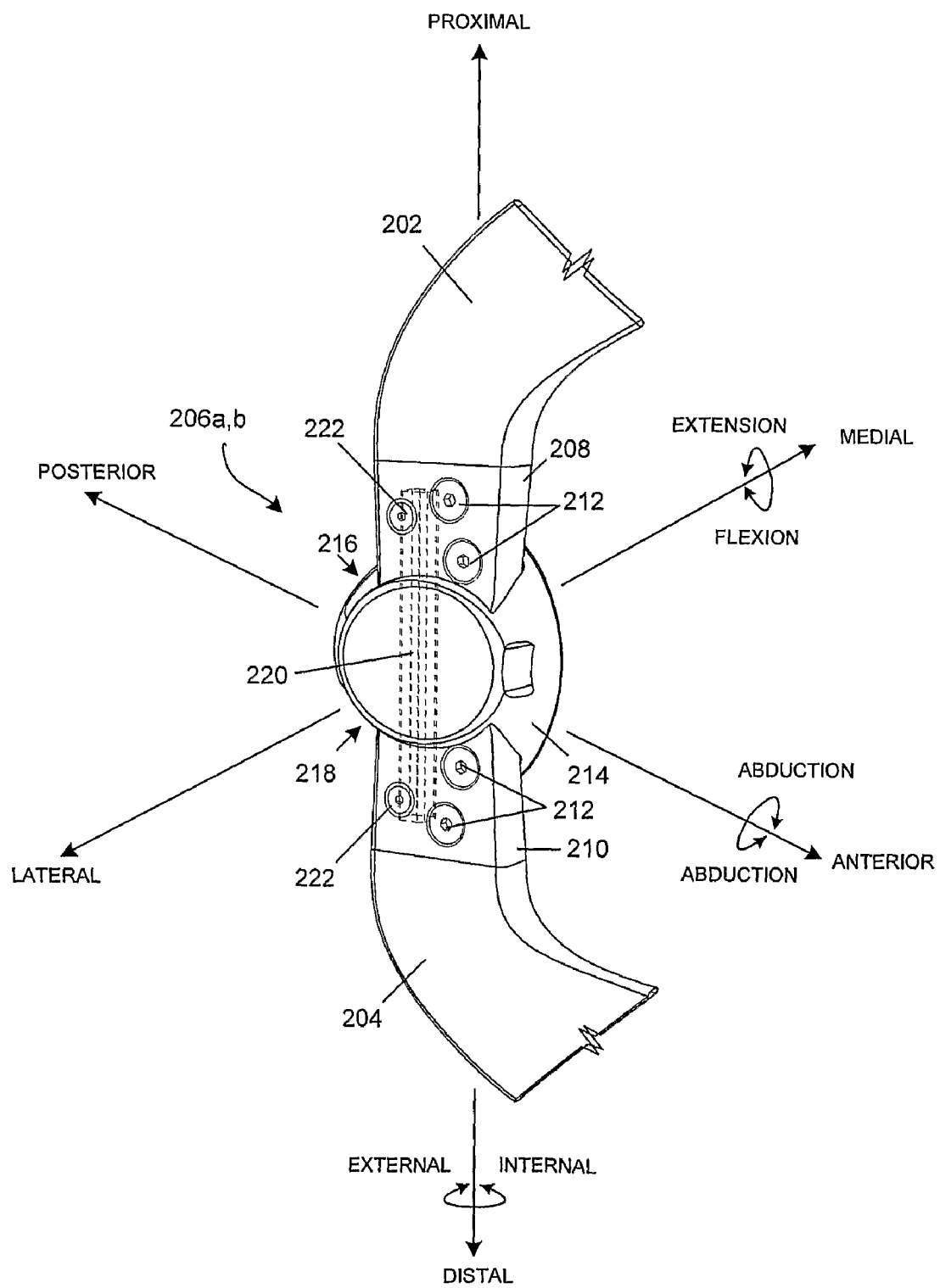
FIG. 10 is a schematic perspective view of a movable joint of the knee brace of FIG. 9.

FIG. 9 illustrates a knee brace 200 having upper and lower leg support frames 202, 204 connected by two movable joints 206a, 206b. The upper and lower leg support frames 202, 204 can be adapted to be secured to the upper and lower leg by, for example, straps and hook and loop fasteners (not shown). Each movable joint 206a, 206b includes two arms 208, 210 respectively connected at one end to the upper and lower leg support frames 202, 204 via screws 212. The other end of each arm 208, 210 is received in a body 214. Referring to FIG. 10, the arms 208, 210 are connected in apertures 216, 218 of the body 214 by a resilient connector 220 which is depicted in phantom. The resilient connector 220 is releasably connected to the ends of the arms 208, 210 by screws 222 which allow the arms 208, 210 to be readily disconnected from and connected to the body 214.

The upper and lower leg support frames 202, 204 can be manufactured by, for example, moulding. The upper and lower leg support frames 202, 204 can be manufactured from, for example, fibreglass, with or without reinforcements. Reinforcements, if used, can include glass cloth or fibres, graphite fibres, Kevlar (trade mark) fibres and Spheretex (trade mark) fibres. Other suitable manufacturing methods and materials will be apparent to those skilled in the art. The body 214 and/or the arms 208, 210 can be manufactured from the same materials as the body 102 and/or the arms 110, 112, as discussed hereinbefore. The resilient connector 220 can be manufactured from the same materials as the resilient connector 114, as discussed hereinbefore.

Each movable joint 206a, 206b is customised to simulate natural anatomical movement of a human knee joint in up to six degrees of freedom. The six degrees of freedom of the human knee include three rotational degrees—flexion/extension, abduction/adduction, internal/external—and three translation degrees—anterior/posterior, medial/lateral, proximal/distal. In use, the movable joints 206a, 206b have the same general functionality as the generic movable joint 100, as discussed hereinbefore.

Figure 11:
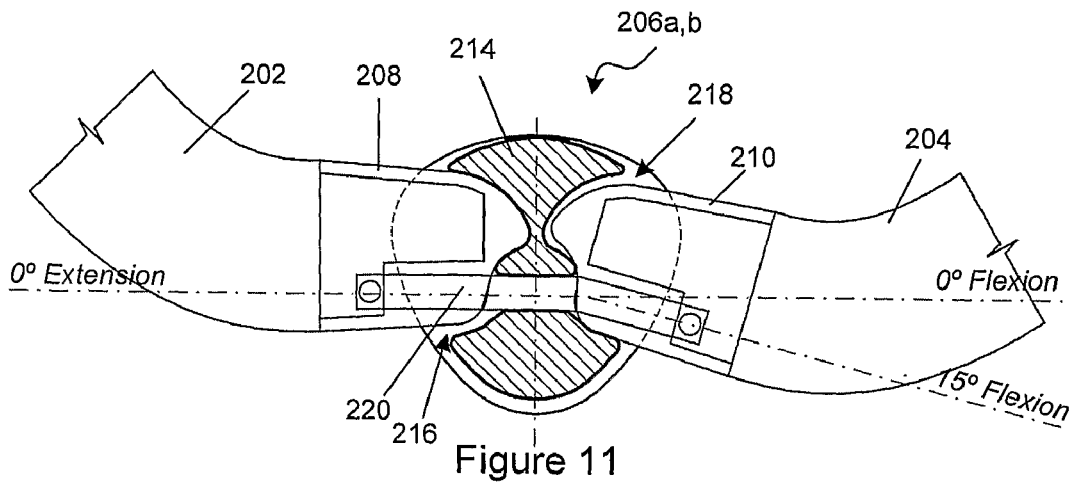
FIGS. 11-13 are schematic partial sectional views of embodiments of the movable joint of FIG. 10 having different internal geometries.
Figure 12:
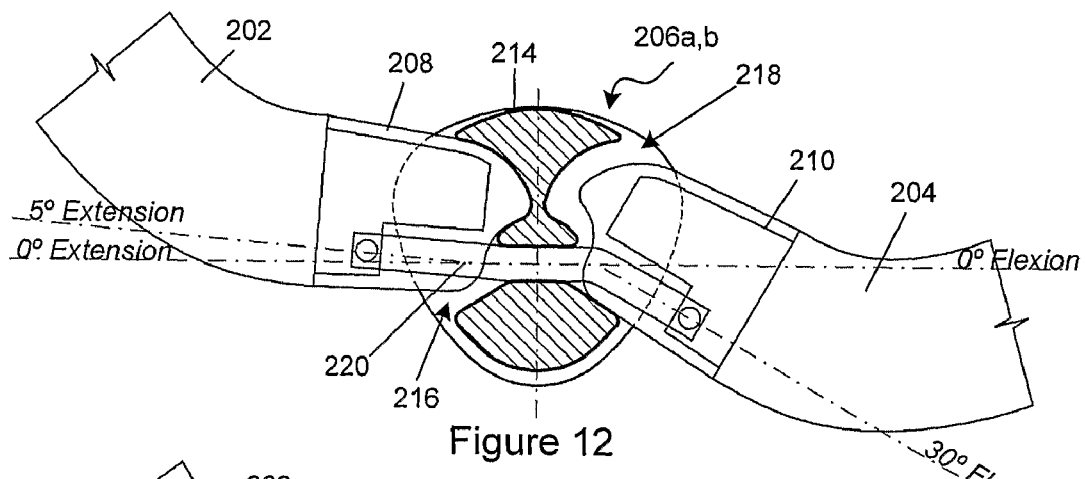
Figure 13:
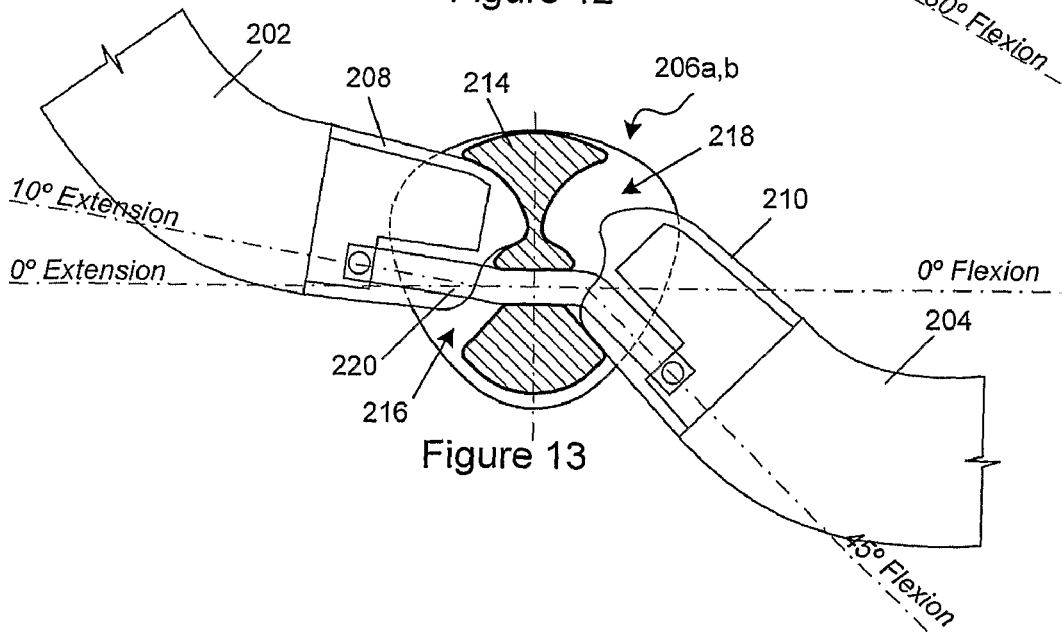
Figure 14:
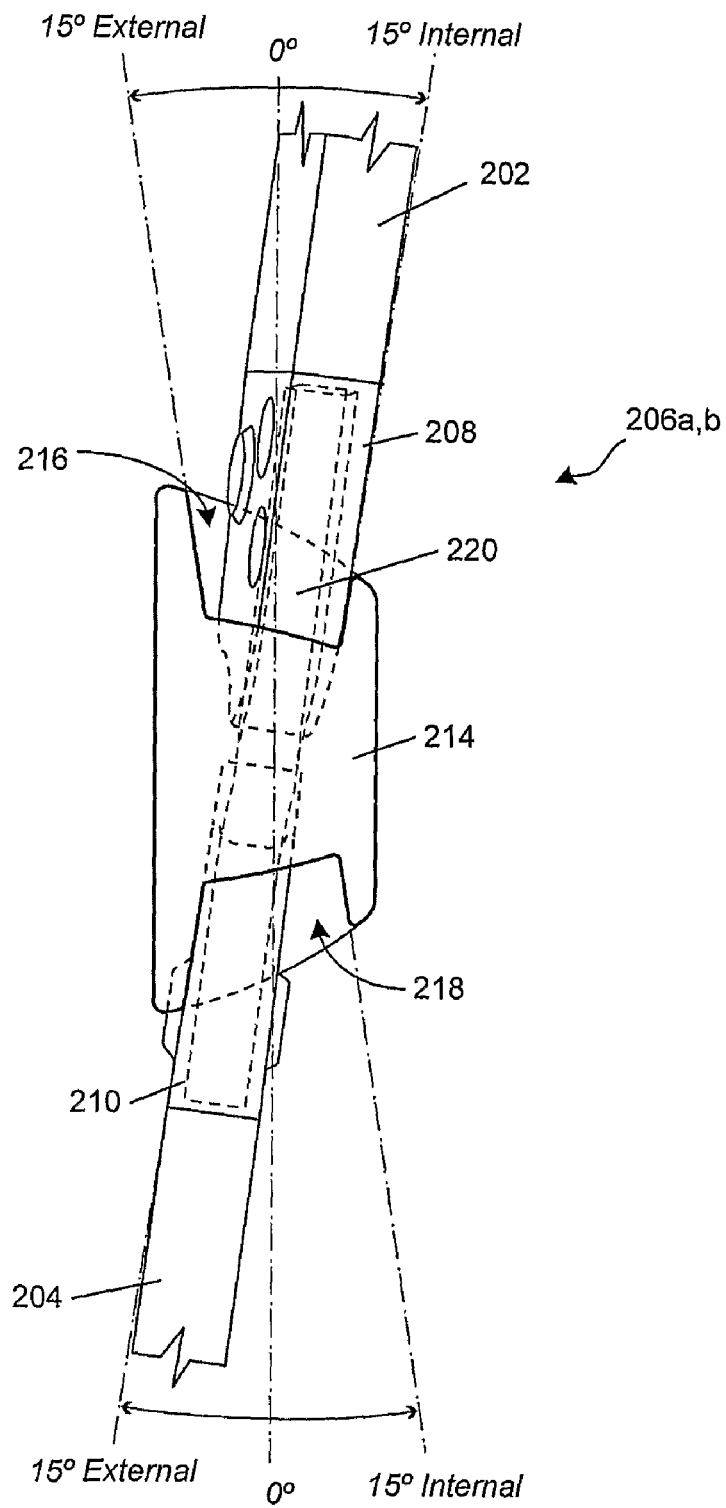
FIG. 14 is a schematic top view of an embodiment of the movable joint of FIG. 10.

The independent movement of the arms 208, 210 in up to six degrees of freedom can be customised by controlling the geometry of the apertures 216, 218 and/or the abutting ends of the arms 208, 210, and/or by controlling the resilience characteristics of the resilient connector 220. FIGS. 11-14 depict embodiments of the body 214 with apertures 216, 218 having different example geometries for controlling the range of movement of the knee brace 200 in up to six degrees of freedom. FIG. 11 is a cross-section of an embodiment of the body 214 in which the apertures 216, 218 are shaped to control the range of flexion and extension of the knee brace 200 from approximately 0 degrees extension to approximately 15 degrees of flexion. FIG. 12 depicts an alternative cross-section of the body 214 in which the apertures 216, 218 are shaped to control the range of flexion and extension of the knee brace 200 from approximately 5 degrees extension to approximately 30 degrees of flexion. In a further embodiment illustrated in FIG. 13, the apertures 216, 218 have been shaped to control the range of flexion and extension from approximately 10 degrees extension to approximately 45 degrees of flexion. FIG. 14 is a top view of an embodiment of the body 214 in which the apertures 216, 218 have been shaped to control internal/external rotation during flexion and extension from approximately 0 degrees to approximately 15 degrees.

The different embodiments of the body 214 depicted in FIG. 11-14 can comprise a movable joint system in which the apertures 216, 218 of each body 214 are differently shaped to the apertures 216, 218 of other bodies 214. In such a system, the arms 208, 210 are capable of being readily disconnected from and connected to the different bodies 214 via the screws 222 to limit independent movement of the arms 208, 210 at different selected angles of flexion and extension. The different bodies 214 may therefore be interchanged so that any given movable joint 206a, 206b is tailored to the needs of a wearer of the knee brace 200. For example, if the movable joint system is used in a orthopaedic knee brace 200 worn by a patient, the different bodies 214 may be changed as the needs of the patient change. Thus, if the needs of the patient change, the bodies 214 may be changed accordingly. Conversely, if the same knee brace 200 is to be re-used with a different patient, the limits of independent movement of the arms 208, 210 in up to six degrees of freedom may be easily modified by simply interchanging the bodies 214 to meet the needs of the second patient.

Figure 15:
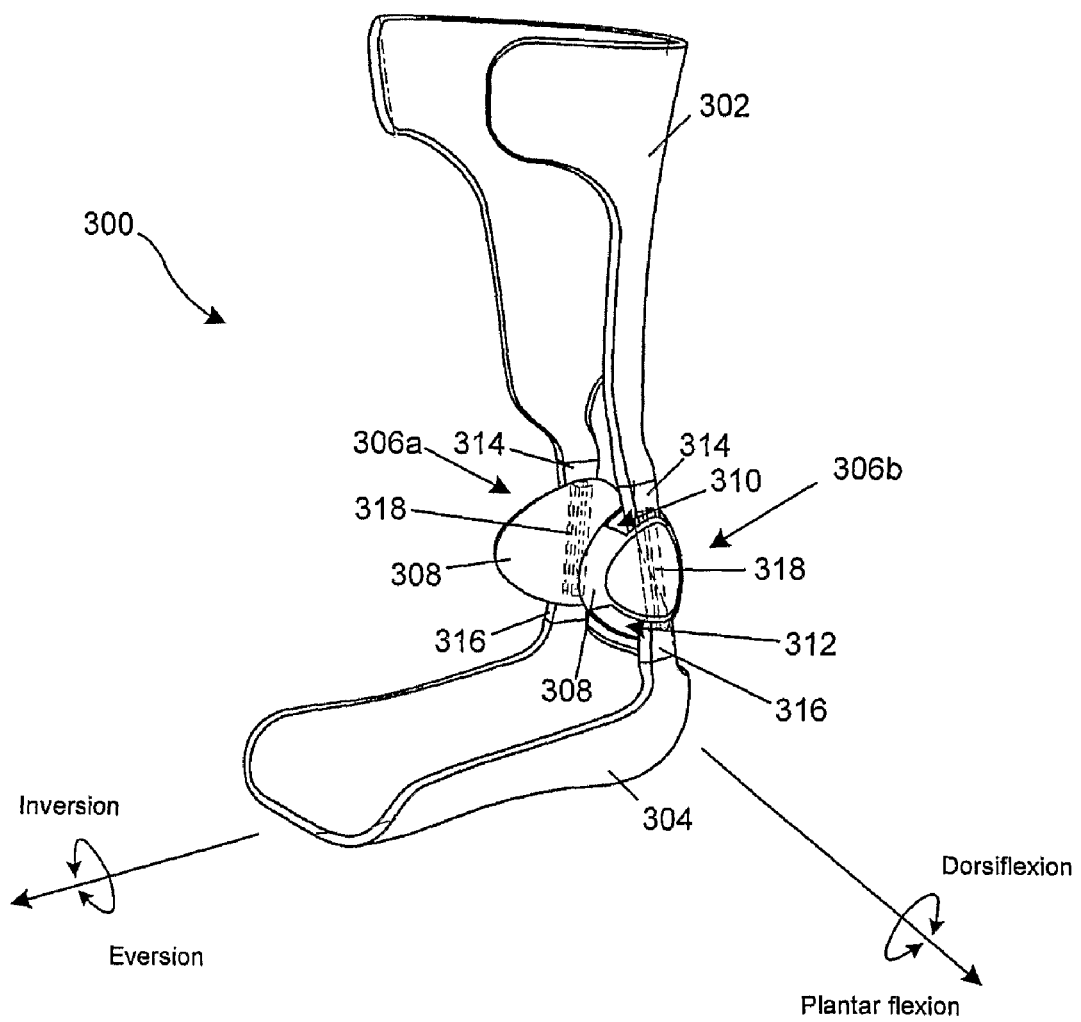
FIG. 15 is a schematic perspective view of an ankle brace including embodiments of a movable joint of the present invention.

FIG. 15 illustrates an ankle brace 300 having a lower leg support frame 302 and a foot support frame 304 connected by two movable joints 306a, 306b. The lower leg and foot support frames 302, 304 can be adapted to be secured to the lower leg and the foot by, for example, straps and hook and loop fasteners (not shown). The components of the ankle brace 300 and the movable joints 306a, 306b have the same general construction and composition as the knee brace 200 and the movable joints 206a, 206a, as discussed hereinbefore. Each movable joint 306a, 306b therefore generally includes a body 308 having two apertures 310, 312 receiving two arms 314, 316 connected by a resilient connector 318. However, the shape of the abutment portions of the apertures 310, 312 and the abutting ends of the arms 314, 316 of the movable joints 306a, 306b is customised to control the movement of the lower leg support frame 302 and the foot support frame 304 in several degrees of freedom corresponding to the natural anatomical movement of the human ankle. The degrees of freedom of the ankle include dorsiflexion, plantar flexion, inversion and eversion. Dorsiflexion is movement in which the foot is pivoted toward the leg. Plantar flexion is movement in which the foot is pivoted away from the leg. Inversion is movement when the foot turns inwards, and eversion is movement when the foot rotates outwards. In use, the geometry of the apertures 310, 312 allows dorsiflexion and plantar flexion of the ankle brace 300 while controlling inversion, eversion and twisting.

It will be understood that embodiments of the present invention provide a simple, low cost movable joint having up to six degrees of freedom which is capable of absorbing shocks, vibrations and loads. Such a movable joint has many potential uses including, but not limited to, use in human or animal joint support devices. Embodiments of the movable joint of the present invention can have essentially any shape and can be made completely from polymers or polymer blends.

The present invention is not limited to the embodiments that have been described and depicted, but variations and modifications may be made without departing from the scope of the present invention.

Claims defining the invention are as follows:

1. A movable joint comprising:
a body having two spaced apertures connected by an opening;
two arms having ends receivable in the apertures; and
a resilient connector, having a resilience, passing through the opening to connect the ends of the arms in the apertures, wherein the resilience of the resilient connector:
allows independent movement of the arms in up to six degrees of freedom which is controlled by engagement of abutment portions of the arms with respective abutment portions of the apertures, and
absorbs forces applied to the arms.

2. A movable joint according to claim 1, wherein the independent movement of the arms in up to six degrees of freedom is controlled by selection of one or a combination of: a three-dimensional shape of the abutment portions of the arms, a three-dimensional shape of the abutment portions of the apertures, and by selection of the resilience characteristics of the resilient connector.

3. A movable joint according to claim 2, wherein the independent movement of the arms in up to six degrees of freedom is controlled of substantially simulating-anatomical movement of a human or animal joint in up to six degrees of freedom.

4. A movable joint according to claim 1, wherein the resilient connector is pretensioned to resist tensile loads applied to the arms.

5. A movable joint according to claim 4, wherein the resilient connector includes a pretensioned element provided inside a resilient member.

6. A movable joint according to claim 1, wherein the resilient connector releasably connects the ends of the arms in the apertures.

7. A movable joint system according to claim 1, in combination with a joint support device for a human or animal joint, the joint support device including two support portions connected for relative movement about the human or animal joint by at least one movable joint.

8. A movable joint system according to claim 7, wherein the joint support device is a human knee brace and the two support portions are upper and lower leg portions.

9. A movable joint system according to claim 7, wherein the joint support device is a human ankle brace and the two support portions are a lower leg portion and a foot portion.

10. A movable joint system according to claim 1, in combination with a joint support device for a human or animal joint, the joint support device including two support portions connected for relative movement about the human or animal joint.

11. A movable joint system according to claim 10, wherein the joint support device is a human knee brace and the two support portions are upper and lower leg portions.

12. A movable joint system according to claim 10, wherein the joint support device is a human ankle brace and the two support portions are a lower leg portion and a foot portion.

13. A movable joint system comprising:
a plurality of bodies each having two spaced apertures connected by an opening;
two arms having ends receivable in the apertures; and
a resilient connector, having a resilience, passing through the opening to releasably connect the ends of the arms in the apertures, wherein the resilience of the resilient connector:
allows independent movement of the arms in up to six degrees of freedom which is controlled by engagement of abutment portions of the arms with respective abutment portions of the apertures; and
absorbs forces applied to the arms;
wherein the abutment portions of the apertures of each body are differently shaped to the abutment portions of the apertures of other bodies, whereby the independent movement of the arms in up to six degrees of freedom is selectively controllable by interchanging the bodies.

14. A movable joint comprising:
a single unitary body;
two spaced apertures in the body;
an opening inside the body interconnecting the two apertures;
two arms each having one end movably received in one of the two apertures; and
an elongate resilient connector extending through the opening with opposite ends interconnecting the one ends of the two arms.

15. A movable joint according to claim 14, wherein the body is made of plastic.

16. A movable joint according to claim 14, wherein the resilient connector comprises a pretensioned fibre spine overmoulded by a resilient plastic member.

17. A movable joint according to claim 14, wherein the resilient connector has a selected resilience that, in use, influences relative movement of the two arms.

18. A knee brace comprising two movable joints according to claim 14.

19. An ankle brace comprising two movable joints according to claim 14.

* * * * *